(12) United States Patent
Sridharan et al.

(10) Patent No.: US 6,743,388 B2
(45) Date of Patent: Jun. 1, 2004

(54) PROCESS OF MAKING POLYMER ARTICLES

(75) Inventors: Srinivasan Sridharan, Morgan Hill, CA (US); Murthy V. Simhambhatla, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 91 days.

(21) Appl. No.: 10/038,816

(22) Filed: Dec. 31, 2001

(65) Prior Publication Data

US 2003/0124279 A1 Jul. 3, 2003

(51) Int. Cl.[7] .......... B29C 55/04; B29C 67/20; D01D 5/04; D01D 5/12; D01D 5/247
(52) U.S. Cl. .......... 264/205; 264/210.5; 264/210.8; 264/211.13; 264/211.14; 264/235.6; 264/291; 264/346
(58) Field of Search .............. 264/205, 210.5, 264/210.8, 211.13, 211.14, 235.6, 291, 346

(56) References Cited

U.S. PATENT DOCUMENTS

| | | |
|---|---|---|
| 3,426,754 A | 2/1969 | Bierenbaum et al. |
| 3,679,538 A | 7/1972 | Druin et al. |
| 3,953,566 A | 4/1976 | Gore |
| 3,962,153 A | 6/1976 | Gore |
| 4,187,390 A | 2/1980 | Gore |
| 4,344,908 A | 8/1982 | Smith et al. |
| 4,356,138 A | 10/1982 | Kavesh et al. |
| 4,384,023 A | 5/1983 | Okamura et al. |
| 4,413,101 A | 11/1983 | Schmidt et al. |
| 4,536,536 A | 8/1985 | Kavesh et al. |
| 4,655,769 A | 4/1987 | Zachariades |
| 5,374,473 A | 12/1994 | Knox et al. |
| 5,433,909 A | 7/1995 | Martakos et al. |
| 5,643,511 A | 7/1997 | Pluyter et al. |
| 6,120,477 A | 9/2000 | Campbell et al. |
| 6,238,408 B1 | 5/2001 | Kawabata et al. |
| 6,395,208 B1 | 5/2002 | Herweck et al. |

FOREIGN PATENT DOCUMENTS

| | | |
|---|---|---|
| EP | 0 662 388 A2 | 7/1995 |
| WO | WO 86/02656 A1 | 5/1986 |
| WO | WO 91/01210 A1 | 2/1991 |
| WO | WO01/45766 A1 | 6/2001 |

OTHER PUBLICATIONS

Hill, M.J., et al., *Direct Evidence for Distinctive, Stress–Induced Nucleus Crystals in the Crystallization of Oriented Polymer Melts*, Journal of Macromolecular Science, pp. 153–169, Mar. 1969.

Keller, A., *Unusual Orientation Phenomena in Polyethylene Interpreted in Terms of the Morphology*, Journal of Polymer Science, vol. XV, pp. 31–49, 1955.

(List continued on next page.)

*Primary Examiner*—Leo B. Tentoni
(74) *Attorney, Agent, or Firm*—Fulwider Patton Lee & Utecht, LLP

(57) ABSTRACT

A method including forming a semi-crystalline polymer material into a lamella; and stretching the lamella into a polymer including a node of folded lamella and a fibril orientation. A method including extruding a pseudo-gel including an ultrahigh molecular weight polyethylene material into a lamella; stretching the lamella into a polymer including a node of folded lamella and a fibril orientation; and annealing the polymer at a temperature sufficient to define the node and fibril orientation. An apparatus including a body portion formed of a dimension suitable for a medical device application and including a semi-crystalline polymer arrayed in a node of folded lamella and a fibril orientation. An apparatus including a body portion including an ultrahigh molecular polyethylene material arrayed in a node of folded lamella and a fibril orientation.

14 Claims, 4 Drawing Sheets

OTHER PUBLICATIONS

Smook, Jan, et al., *Elastic Flow Instabilities and Shish–kebab Formation During Gel–Spinning of Ultra–High Molecular Weight Polyethylene, Journal of Materials Science*, vol. 19, pp. 31–43, 1984.

Sprague, B.S., *Relationship of Structure and Morphology to Properties of "Hard" Elastic Fibers and Films, Journal of Macromolecular Science*, vol. B6 (1–2), pp. 157–187, 1973.

Van Hutten, P.F., et al., *Shish–Kebabs as an Intermediate Morphology in Gel–Spinning/Hot–Drawing of Polyethylene, Polymer Communications*, vol. 24, Aug. 1983.

Van Hutten, P.F., et al., *The Deformation Behaviour of Polyethylene Shish–Kebabs Produced by Stirring–Induced Crystallization, Colloid and Polymer Science*, vol. 262, No. 7, pp. 521–525, 1984.

Van Hutten, P.F., et al., *The Plastic Deformation of Ultra–High Molecular Weight Polyethylene, Journal of Materials Science,*, vol. 20, pp. 1556–1570, 1985.

Murthy, N.S., et al., *Structural Changes Prior to Melting in Extended–Chain Polyethylene Fibres, Polymer Communications*, vol. 31, pp. 50–52, Feb. 1990.

US 6,743,388 B2

PROCESS OF MAKING POLYMER ARTICLES

BACKGROUND

1. Field

The invention relates to polymer processing and more particularly to the formation of polymer products used in a variety of applications.

2. Background

Polymer constructs with a balance of porosity, strength, flexibility and chemical inertness or biocompatibility are desired in many biomedical and industrial applications.

In medical implant fields, polymers such as Dacron polyester and expanded polytetrafluoroethylene (ePTFE) have been used for medium and large diameter vascular prosthesis. Dacron prosthesis are generally woven or knitted into tubular constructs. The relatively large pore size resulting from knitting and weaving techniques allows blood to pass through these pores, necessitating either pre-clotting these constructs with the patient's blood before implantation, or impregnating the constructs with a biocompatible filler. The porosity of ePTFE can be tailored by adjusting the node and fibril structure, and consequently the porosity and pore size, such that blood is contained within the tubular structure under physiological conditions. Neither Dacron, nor ePTFE tubular constructs has however functioned effectively as small diameter vascular prostheses due to problems of thrombosis and anastomotic hyperplasia.

The flexibility, strength, biostability and ability to adjust porosity has also led to ePTFE being used for tissue augmentation in plastic surgery, in dura mater repair in neurosurgery, and for breathable, moisture-barrier cast liners.

In the medical device industry, angioplasty balloons are typically formed from polyethylene terephthalate, nylon, segmented polyurethanes. To reduce the effective profile of the device for ease of delivery into the vasculature, balloons are folded on to the catheters. Upon inflation in the vasculature, the balloons unfold to assume a cylindrical profile. This unfolding generates non-uniform stresses in lesions during inflation. Furthermore, when stents are mounted on folded balloons, their deployment in the vasculature may be non-uniform due to the unfolding process. There is consequently a need for a balloon that is flexible, yet strong with the ability to be delivered in the vasculature in a small tubular profile without folding. Materials with node and fibril structures, that can be rendered auxetic, i.e., having a negative Poisson's ratio, with appropriate processing are particularly suitable for this application. Poisson's ratio In the field of local drug delivery, there is a need for chemically inert and biocompatible microporous drug reservoirs for releasing drugs from transdermal patches. Polymers such as ultrahigh molecular weight polyethylene (UHMWPE) may serve this need if they are rendered porous.

In the textile industry, ePTFE barrier layers are used for apparel that needs to be breathable, while preventing moisture from passing through the apparel. The combination of flexibility, lubricity and strength have also led to ePTFE use in dental floss.

UHMWPE is used as a separator membrane for electrochemical cells such as lithium-ion batteries, supercapacitors and fuel cells. For these applications, microporous UHMWPE membranes provide the right balance of porosity, wettability, flexibility and strength.

U.S. Pat. No. 5,643,511 discloses a process for the preparation of microporous UHMWPE by solvent evaporation from a gel-formed film. The films are stretched uniaxially or biaxially either during solvent evaporation or after solvent evaporation, to achieve the desired porosity. The microporous films thus obtained do not have a node and fibril structure.

U.S. Pat. No. 4,655,769 describes a process for preparing microporous UHMWPE by forming a pseudo-gel of UHMWPE sheet in a solvent, extracting the solvent with a more volatile solvent, evaporating the volatile solvent to create a semi-crystalline morphology and stretching the dry sheet. These films do not exhibit a well-defined node and fibril structure.

In regards to the above applications and limitations of current materials, there remains a desire for porous and flexible polymer constructs having high strength, good chemical inertness and biocompatibility, and which can preferably be made to exhibit auxetic behavior.

SUMMARY

A method is disclosed. The method includes, in one embodiment, forming a semi-crystalline polymer material into a lamella, and stretching the lamella into a polymer article including a node of folded lamella and a fibril orientation. Such polymer article may be used in a variety of applications including, but not limited to, medical device applications such as in catheter balloons, and various grafts. Other applications include, but are not limited to, use in dental floss, sutures, filters, membranes, drug delivery patches, and clothing.

Ultra high molecular weight polyethylene is one example of a suitable semi-crystalline polymer material. In another embodiment, a method including extruding a pseudo-gel comprising an ultrahigh molecular weight polyethylene material into a lamella, stretching the lamella into a polymer including a node of folded lamella and a fibril orientation, and annealing the polymer at a temperature sufficient to define the node and fibril orientation.

An apparatus is still also disclosed. In one embodiment, the apparatus includes a body portion formed of a dimension suitable for a medical device application and including a semi-crystalline polymer arrayed in a node of folded lamella and a fibril orientation or microstructure. In another embodiment, an apparatus including a body portion comprising an ultra-high molecular weight polyethylene material arrayed in a node of folded lamella and a fibril orientation.

DETAILED DESCRIPTION

Figure 1:
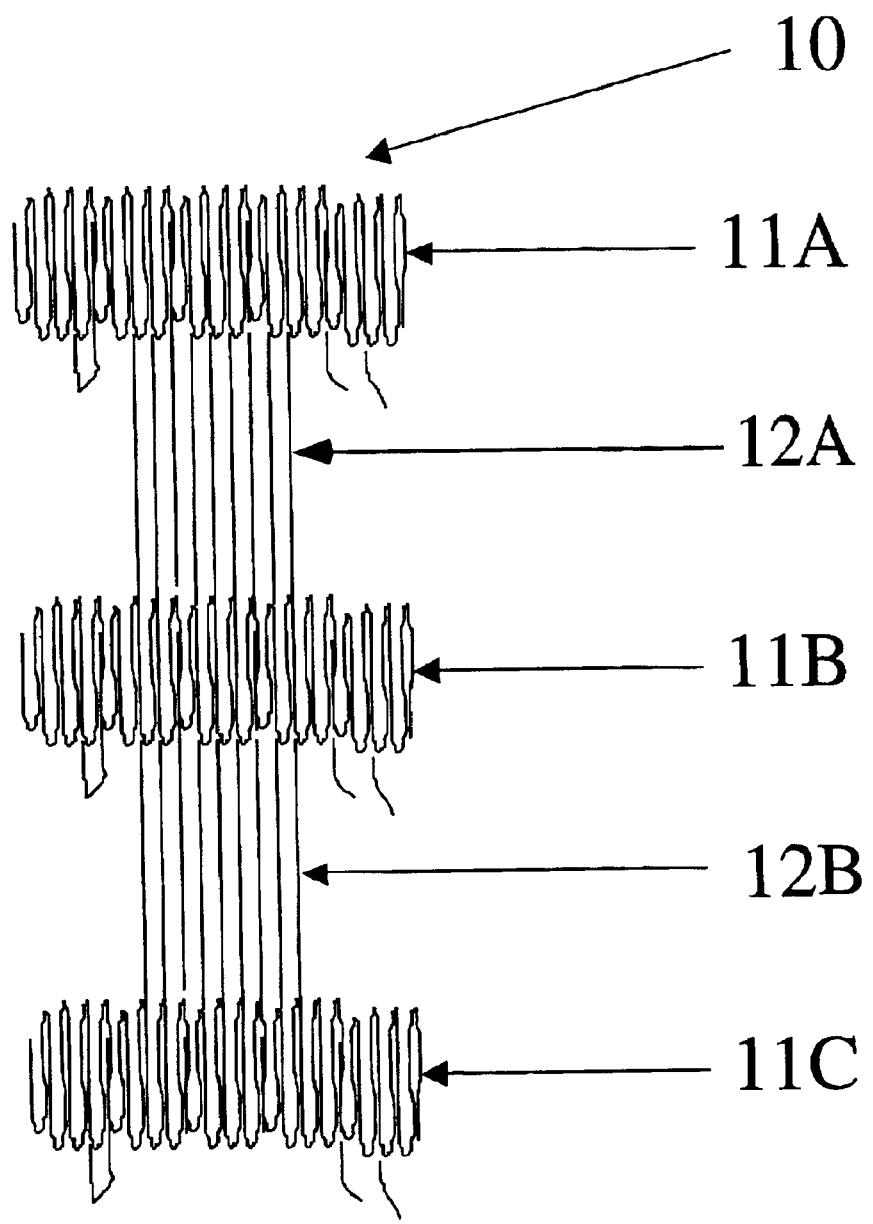
FIG. 1 shows a schematic top perspective view of a polymer array in a node of folded lamella and fibril orientation.

FIG. 1 shows a polymer product formed according to the techniques described herein. The polymer product as shown in FIG. 1 is a portion of a polymer fiber having a "shish kebab" morphology formed from a semi-crystalline polymer crystallized from the melt state under high stress/strain fields. These polymers "row nucleate" with rows parallel to a draw direction (e.g., of an extruder) and a crystallite growth perpendicular to the direction of the draw. Highly anisotropic crystallites with extended chain cores surrounded by chain-folded lamella result.

FIG. 1 shows polymer structure 10 of node 11A, 11B, and 11C. Each node as described is formed of folded lamella. Between nodes in FIG. 1 are fibril portions 12A and 12B formed by, in one example, applying a tensile force to an extruded polymer (e.g., an extruded polymer fiber) in the direction of the draw of an extruder (e.g., stretching). In effect, the tensile force pulls a portion of the polymer from the folded lamella resulting in a folded portion (node 11A, 11B, 11C and a fiber-like portion (fibril portions 12A, 12B).

In one embodiment, polymer structure 10 is a semi-crystalline polymer material. Such semi-crystalline polymers include polyalkylene polymers, polyolefin polymers, and polyoxymethylene-acetyl co-polymers. Particular types of polyalkylene polymers include polypropylenes and polyethylenes. Particular preferred polymers are high molecular weight or ultra-high molecular weight polyethylene (UHMWPE).

Suitable semi-crystalline polymers are those polymers that are generally not suitable for melt extrusion due to the viscosity of the polymer inhibiting the melt flow. Suitable polymers, such as polyethylene have molecular weights in the range of about 1 million grams per mole (gms/mole) to about 10 million gms/mole. This corresponds to a weight average chain length of $3.6 \times 10^4$ to $3.6 \times 10^5$ monomer units or $7 \times 10^4$ to $7 \times 10^5$ carbons. Polypropylene should have similar backbone carbon chain lengths. UHMWPE polymers are classified by molecular weight determination detailed in American Society for Testing Methods (ASTM) D1601 and D4020. Particularly, suitable polyethylene should have a molecular weight of at least about 500,000 gms/mole, preferably at least about 1,000,000 gms/mole, and more preferably at least about 2,000,000 gms/mole to about 10,000,000 gms/mole. Polymers that are commercially available in powder form that are suitable are GUR 4150™, GUR 4120™, GUR 2122™, GUR 2126™ manufactured by Ticona; Mipelon XM 220™ and Mipelon XM 221U™ manufactured by Mitsui; and 1900™, HB312CM™, HB320CM™ manufactured by Montell. Suitable polypropylenes have a molecular weight of at least 500,000 gms/mole, preferably at least about 1,000,000 gms/mole and more preferably at least about 2,000,000 gms/mole to about 10,000,000 gms/mole.

Figure 2:
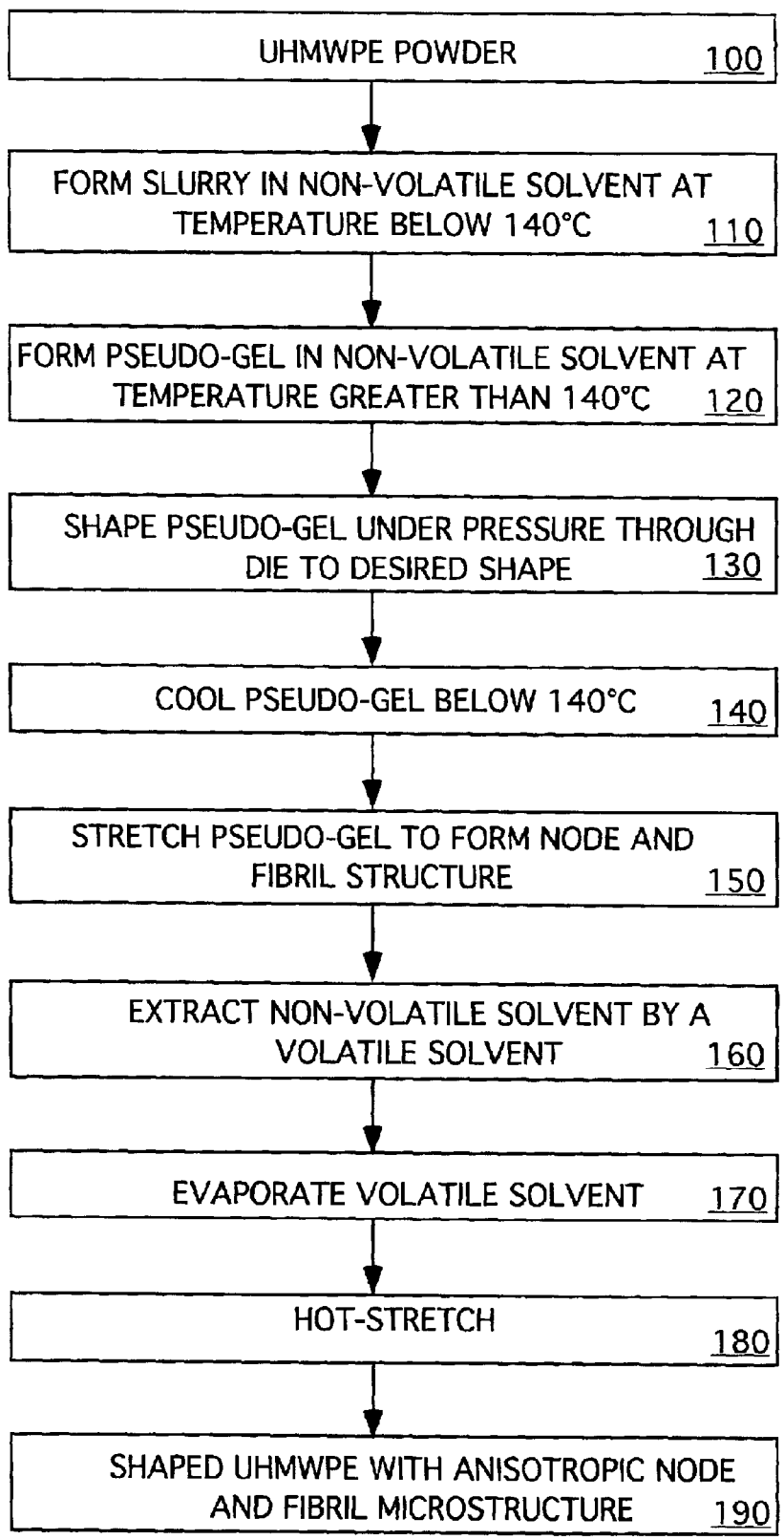
FIG. 2 is a flow chart of a process for making a polymer product using a non-volatile first solvent and a low boiling second solvent.

FIG. 2 describes a process for forming a polymer product having a desired node and fibril morphology. The polymer in this example is UHMWPE. In one embodiment as shown in FIG. 2, porous UHMWPE may be prepared from the starting UHMWPE powder (block 100) by forming a slurry in a first non-volatile solvent, such as mineral oil or paraffin oil (such as Hydrobrite 550, Hydrobrite 380, Hydrobrite 1000 manufactured by Witco Corporation) at a temperature below about 140° C., and preferably below about 120° C. and more preferably below about 100° C., but above about 25° C. (block 110). The weight percent of the polymer is in the range of about one weight percent (wt %) to about 50 wt % and preferably in the range of about one wt % to about 30 wt % and more preferably in the range of about five wt % to about 20 wt %. It is appreciated that additives may also be added to the slurry. Suitable additives include, but are not limited to, antioxidants such as Irgonox-antioxidants to inhibit oxidation.

The slurry of polymer powder and solvent (and optional additive(s)) is then taken to a temperature above about 140° C. to about 325° C., preferably from about 180° C. to about 275° C. to form a pseudo-gel using a mixing device, such as a stirred vessel or a single screw extruder or a twin-screw extruder or a pipe with static mixers or a ram extruder (block 120). A pseudo-gel in this context may be thought of as having gel-like properties, typically without (or with less of) the cross-linking behavior seen in true gels. The pseudo-gel thus formed is then pushed under pressure of about 500 pounds per square inch (psi) to about 10,000 psi through a die to form the desired final shape of the product, such as a fiber, or film, or tape (block 130).

The shaped pseudo-gel thus formed is then cooled using a cooling medium such as air or water to a temperature below about 140° C., and preferably below about 100° C., more preferably below about 30° C. and most preferably below about 20° C. (block 140). The reduced temperature tends to cause folded chain row-nucleated structures to form in the microstructure. These structures are then stretched at a temperature below about 50° C. and preferably below about 40° C. and more preferably below about 30° C. to induce fibrillation (block 150). The stretch ratio is preferably from about 2:1 to about 20:1. The amount of stretching eventually determines the porosity of the polymer article formed. Optionally, the stretching may be done after the extraction of the first non-volatile solvent by a second volatile solvent (block 160) and the evaporation of the second volatile solvent (block 170). During stretching, the porosity and the orientation of the crystals may be increased due to stretching of the article. Additionally, an optional step of hot stretching (block 180) such as on the order of 130° C. to 150° C. may be added to increase porosity or increase mechanical properties by increasing crystalline and amorphous orientation. It is believed that hot stretching will also result in a modification of the folded chain lamellar structure of the crystallites. The result is a shaped UHMWPE porous article (block 190). The porosity of the final article is preferably at least about 10% by volume and more preferably at least about 30% by volume.

Figure 3:
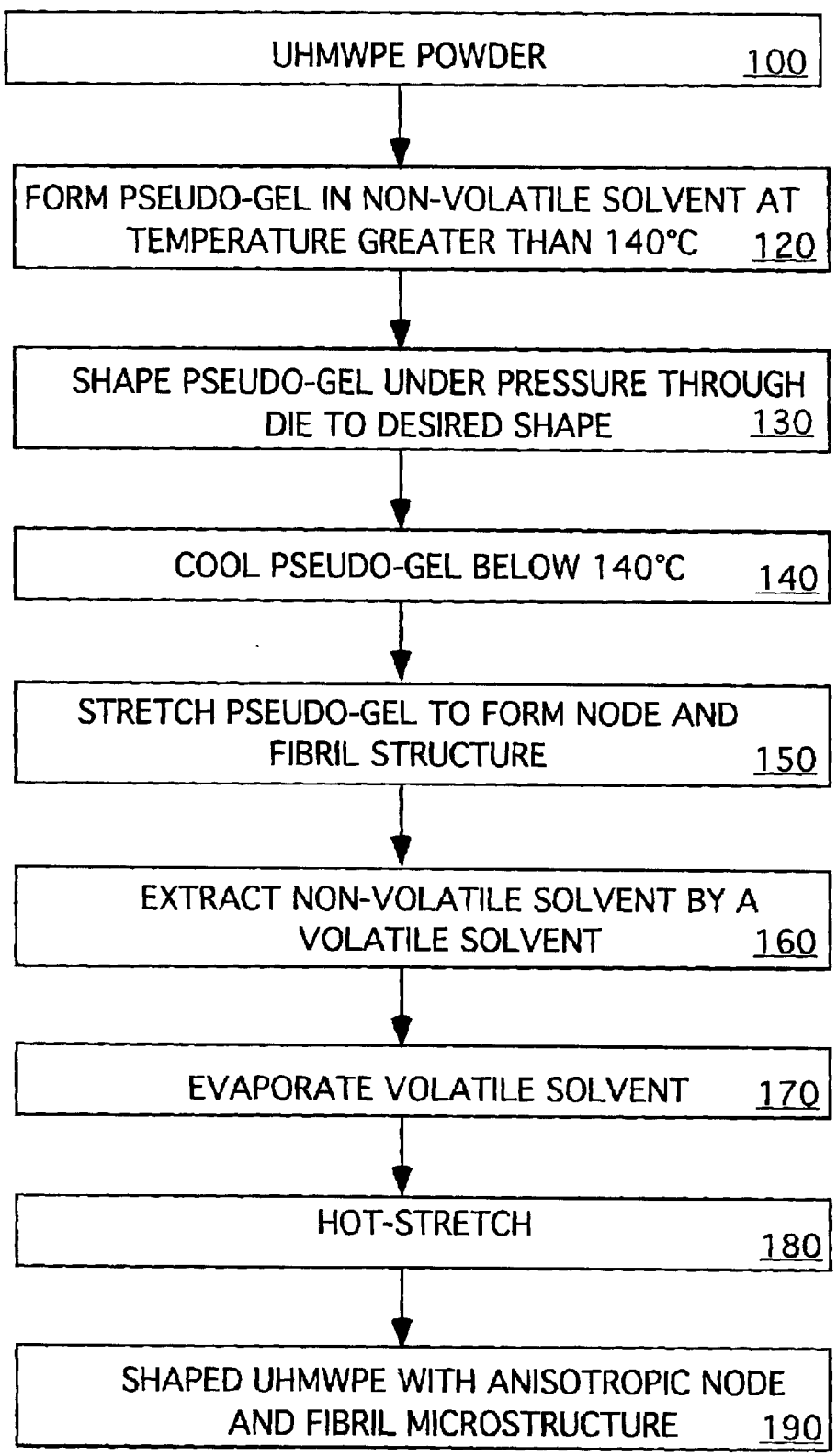
FIG. 3 is a flow chart of an alternative process for making a polymer product using a non-volatile first solvent and a low boiling second solvent.

An alternative embodiment of making an article starting with the UHMWPE powder is shown in FIG. 3. Starting from a UHMWPE powder (block 100), the UHMWPE is mixed with a first non-volatile solvent such as mineral oil or paraffin oil to form a pseudo-gel inside a mixing device such as a stirred tank, a single screw extruder, a twin-screw extruder, a pipe with static mixers or a ram extruder, at a temperature greater than about 140° C. to about 325° C., preferably greater than about 180° C. to about 275° C. (block 120). The weight percent of the polymer is in the range of about one wt % to about 50 wt % and preferably in the range of about one wt % to about 30 wt % and more preferably in the range of about five wt % to about 20 wt %.

The pseudo-gel is then pushed under pressure of about 500 psi to about 10,000 psi through a shaping die to form the desired shape (block 130). Then, the article is cooled using a cooling medium such as air or water to a temperature below about 140° C., and preferably below about 100° C., more preferably below about 30° C. and most preferably below about 20° C. (block 140). The cooling tends to cause folded chain row-nucleated structures to form in the microstructure. These structures are then stretched at a temperature below about 50° C. and preferably below about 40° C. and more preferably below about 30° C. to induce fibrillation (block 150). The stretch ratio is preferably from about 2:1 to about 20:1. The amount of stretching effects the porosity of the resulting polymer product. Optionally, the stretching may be done after the extraction of the first non-volatile solvent by a second volatile solvent (block 160) and the evaporation of the second volatile solvent steps (block 170). During solvent extraction, this porosity and the orientation of the crystals may be increased due to stretching of the article. Additionally an optional hot stretching may be added to increase porosity or increase mechanical properties by increasing crystalline and amorphous orientation (block 180). It is hypothesized that this step will also change the folded chain lamellar structure of the crystallites. The result is the final product of the invention, which is a shaped UHMWPE porous article 190. The porosity of the final article is preferably at least about 10% by volume and more preferably at least about 30% by volume.

Figure 4:
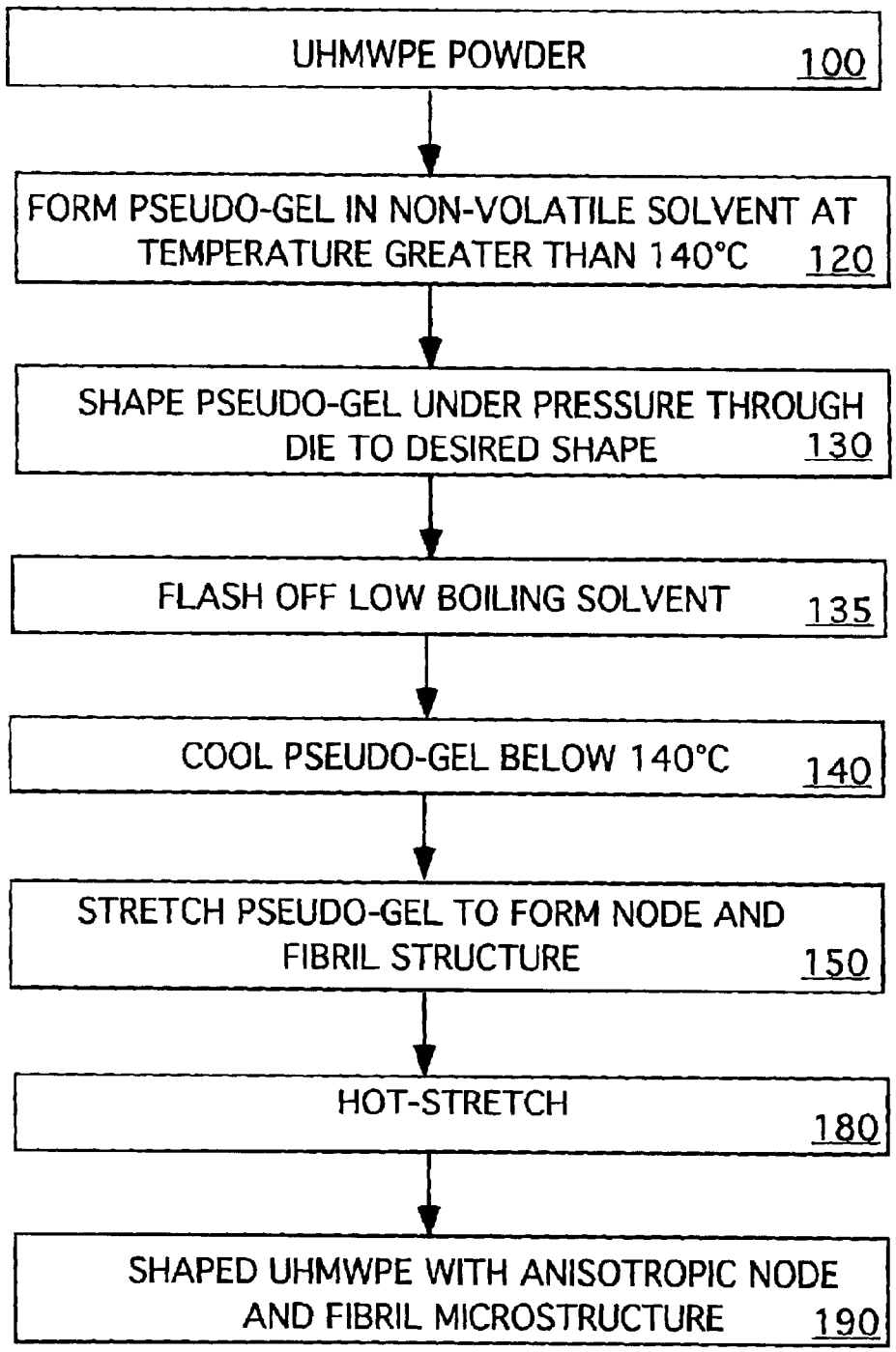
FIG. 4 is a flow chart of a second alternative process for making a polymer product of this invention using a low boiling first solvent.

A third embodiment to make a polymer product of this invention is shown in FIG. 4. In this embodiment, UHMWPE powder (block 100) is mixed with a first solvent such as decalin or p-xylene, inside a mixing device such as a stirred mixer, single screw extrude, twin-screw extruder, a pipe with static mixers or a ram extruder to form a pseudo-gel 120 at a temperature greater than about 140° C. (block 120). The weight percent of the polymer is in the range of one wt % to 50 wt % and preferably in the range of about one wt % to about 30 wt % and more preferably in the range of about five wt % to about 20 wt %. This pseudo-gel with the first solvent is then pushed through a shaping die under a pressure of about 500 psi to about 10,000 psi to make the desired shape such as a fiber or tape of film (block 130). As the shaped pseudo-gel exits the die, the solvent flashes off from the pseudo-gel 135, leaving only a porous UHMWPE, which is cooled, to a temperature below about 140° C., preferably to a temperature below about 100° C. and more preferably to a temperature below about 30° C. using a cooling medium such as air or water (block 140). At this point, folded chain row-nucleated microstructure is formed leading to a porous material. These structures are then stretched at a temperature below about 50° C. and preferably below about 40° C. and more preferably below about 30° C. to induce fibrillation (block 150). The stretch ratio is preferably from about 2:1 to about 20:1. The amount of stretching effects the porosity of the resulting polymer product. Additionally, an optional hot stretching may be added to increase porosity or increase mechanical properties by increasing crystalline and amorphous orientation (block 180). It is hypothesized that the hot stretching will also change the folded chain lamellar structure of the crystallites. The result is a shaped UHMWPE porous article (block 190). The porosity of the final article is preferably at least about 10% by volume and more preferably at least about 30% by volume.

Suitable second solvents used to remove the first non-volatile solvent include hydrocarbons, chlorinated hydrocarbons, cholorofluorinated hydrocarbons and others such as pentane, hexane, heptane, cyclohexane, methylene chloride, trichloroethylene, toluene, carbon tetrachloride, trichlorotrifluoroethylene, diethyl ether and dioxane. Preferred second solvents are those that have atmospheric boiling points below about 90° C., preferably below about 80° C. and more preferably below about 60° C.

The final product has a microstructure as determined by SEM to consist of nodes of about 1 micron to about 100 microns in the largest dimension, which are connected together by means of thin, long polymer fibrils. The internodal distance (IND), which is the distance between the nodes varies from about 10 microns to about 500 microns. In one embodiment the fibrils are oriented in all possible directions, leading to an isotropic structure. In another preferred embodiment, the nodes are about 10 microns to about 25 microns, and the IND is about 25 microns to about 125 microns. In another preferred embodiment, the nodes are about 10 microns to about 25 microns, and the IND is about 200 microns to about 500 microns. The node and fibril microstructure tends to make the polymer exhibit auxetic behavior (i.e., have a negative Poisson's ratio).

In one embodiment the porous UHMWPE product thus formed can be used for medical device application such as catheter balloons, stent grafts, Abdominal Aortic Aneurysm (AAA) grafts, vascular access grafts, pacemaker lead components, guiding catheter liners, Coronary Artery Bypass Grafts (CABG). In addition to these applications, porous UHMWPE can be used in dental floss, sutures, filters, permeable membranes, battery terminal separators, breathable fabrics, ballistic shields, packaging films, and drug delivery patches.

What is claimed is:

1. A method of making a porous ultrahigh molecular weight polyethylene article, comprising:
   a) extruding a pseudo-gel comprising an ultrahigh molecular weight polyethylene polymeric material at a temperature above about 140° C. to form an extruded article;
   b) stretching the extruded article at a temperature below about 50° C. to form a node and fibril microstructure; and
   c) heating the stretched extruded article to anneal the polymeric material at a temperature sufficient to define the orientation of the node and fibril microstructure, to form the porous ultrahigh molecular weight polyethylene article.

2. The method of claim 1, wherein stretching the extruded article comprises stretching at a temperature of up to room temperature.

3. The method of claim 1, wherein prior to stretching the extruded article, the method further comprises quenching the extruded article sufficient to bring the temperature of the extruded article below a melt temperature of the ultrahigh molecular weight polyethylene polymeric material.

4. The method of claim 1, wherein prior to extruding the pseudo-gel, the method comprises:
   forming a pseudo-gel of ultrahigh molecular weight polyethylene material and a solvent.

5. The method of claim 4, wherein the solvent is selected from the group consisting of mineral oil and paraffin oil.

6. The method of claim 4, wherein prior to stretching the extruded article, the method comprises removing a portion of the solvent.

7. The method of claim 4, wherein forming the pseudo-gel comprises, combining the ultrahigh molecular weight polyethylene material with the solvent, wherein the amount of the ultrahigh molecular weight polyethylene material is on the order of 5 to 30 percent by weight.

8. The method of claim 1, wherein the annealing temperature comprises a temperature above the crystalline melting point of the ultrahigh molecular weight polyethylene material.

9. The method of claim 1, wherein the annealing temperature is on the order of 147° C.

10. The method of claim 1, wherein the pseudo-gel is extruded in subpart a) at a temperature above about 180° C. to about 275° C.

11. The method of claim 1, wherein the extruded article is stretched in subpart b) at a temperature below about 30° C.

12. The method of claim 1, wherein extruding the pseudo-gel in subpart a) comprises pressing the pseudo-gel through a die.

13. The method of claim 5, wherein prior to stretching the extruded article, the method comprises extracting the solvent using a volatile solvent and then evaporating the volatile solvent.

14. The method of claim 1, wherein the extruded article stretched in subpart b) is stretched at a temperature below a melt temperature of the ultrahigh molecular weight polyethylene polymeric material, and the node and fibril microstructure comprises a folded chain lamellar structure.

* * * * *